United States Patent [19]

Vermeiren et al.

[11] 4,345,203

[45] Aug. 17, 1982

[54] DEVICE FOR MEASURING THE LUBRICATION OF SURFACES ROLLING OR SLIDING RELATIVE TO EACH OTHER AND LUBRICATED WITH A LUBRICANT

[75] Inventors: Karel N. Vermeiren, Woerden; Rutgerus S. Heemskerk, Vianen; Hendrik Dolfsma, Nieuwegein, all of Netherlands

[73] Assignee: SKF Industrial Trading & Development Company, B.V., Nieuwegein, Netherlands

[21] Appl. No.: 162,953

[22] Filed: Jun. 25, 1980

[51] Int. Cl.$^3$ ............................................. G01R 27/26
[52] U.S. Cl. .................................................. 324/61 R
[58] Field of Search ......................... 324/61 R; 73/64; 340/682

[56] References Cited

U.S. PATENT DOCUMENTS 3,182,255  5/1965  Hopkins et al. ................... 324/61 R
3,331,019  7/1967  Irwin ................................. 324/61 R

FOREIGN PATENT DOCUMENTS 797399  7/1958  United Kingdom ............. 324/61 R
640197  12/1978  U.S.S.R. ........................... 324/61 R Primary Examiner—Stanley T. Krawczewicz
Attorney, Agent, or Firm—Eugene E. Renz, Jr.

[57] ABSTRACT

A device for measuring the lubrication of surfaces which roll or slide relative to one another and are lubricated by a lubricant. The device includes an oscillator generating an AC voltage signal whereby the capacitance between the lubricated surface is measured by first grounding the capacitance and then connecting it by way of a condenser to the output of an oscillator. This output is connected further to a first input of a modulating circuit while the voltage occurring across the capacitance is delivered to a second input of the demodulating circuit. The output of the demodulating circuit is connected to a processing unit which derives a signal corresponding to the thickness of the lubricant film as well as the percentage contact time during a certain interval of measurement from the output signal of the demodulating circuit.

11 Claims, 5 Drawing Figures

DEVICE FOR MEASURING THE LUBRICATION OF SURFACES ROLLING OR SLIDING RELATIVE TO EACH OTHER AND LUBRICATED WITH A LUBRICANT

BACKGROUND AND SUMMARY OF THE PRESENT INVENTION

The invention relates to a device for measuring the lubrication of surfaces rolling or sliding relative to each other and lubricated with a lubricant, equipped with an oscillator generating an AC voltage signal by means of which the capacitance occurring between the lubricated surfaces is measured.

In a known device, the said capacitance is picked up in a capacitive bridge to which the AC voltage signal of the oscillator is supplied. Besides, a measuring circuit is connected to the bridge, delivering an output signal coinciding with the capacitance to be measured. In practice, this known device is found not to function satisfactorily, in part because, with film thicknesses small compared to the surface rugosity, far higher capacitances are measured than the values theoretically to be expected.

The object of the invention is to provide a device of the kind referred to above, in which the disadvantages of the known device are eliminated.

According to the invention, the device is for that purpose characterized in that the said capacitance is firstly grounded and secondly connected by way of a condenser to the output of the oscillator, which output is further connected to a first input of a demodulating circuit, while the voltage occurring across the capacitance is supplied to a second input of the demodulating circuit, the output of the demodulating circuit being connected to a processing unit, which derives a signal corresponding to the thickness of the lubricant film as well as the percentage contact time during a certain interval of measurement from the output signal of the demodulating circuit.

In this way, a device is obtained by means of which simultaneously the thickness of the lubricant film and the percentage contact time during a certain interval of measurement can be measured. Thus it is possible at low values of $\lambda$, where $\lambda$ is the ratio of the thickness of the lubricant film to the surface rugosity, to correct the measured thickness of the film for the measured percentage contact time.

According to the invention, the demodulating circuit may consist of a multiplier and a low-pass filter connected to the output of the multiplier. It is thus brought about that the demodulating circuit delivers an output signal depending exclusively on the thickness of the lubricant film and on time, whence the processing unit can derive the desired measurements in a simple manner.

According to the invention, the processing unit is provided with a circuit forming the reciprocal of the output signal of the demodulating circuit, as well as the first means connected to the output of the reciprocal circuit and delivering an output signal corresponding to the thickness of the lubricant film and an output signal corresponding to the capacitance occurring between the lubricated surfaces.

Advantageously, the processing unit may be provided with second means converting the measured percentage contact time into a correction signal supplied to a second input of the reciprocal signal, in such manner that with increasing percentage contact time, the output signal of the reciprocal circuit decreases. In this way an automatic correction of the thickness measurement of the lubricant film is obtained, thus providing an accurate result of measurement.

Preferably, the voltage occurring across the capacitance present between the lubricated surfaces is delivered to the demodulating circuit by way of a band-pass filter tuned to the oscillator frequency, the oscillator being likewise connected to the demodulating circuit by way of a band-pass filter tuned to the oscillating frequency. In this way any possible network interference deriving from the system to be tested is suppressed. The band-pass filter for the oscillator signal serves to maintain the correct phase relationship between the input signals of the demodulating circuit.

BRIEF DESCRIPTION OF THE DRAWINGS

The invention will now be further illustrated with reference to the drawing, showing an embodiment by way of example.

DESCRIPTION OF THE PREFERRED EMBODIMENT

In the following description of the device according to the invention, the measurement of the lubrication condition of a ball bearing lubricated with oil will be explained as a practical example, but this does not imply that the use of the device is limited to that application.

It is known that the thickness of the oil film in a lubricated ball bearing depends on various factors, among them the rotational speed and the load. The thickness h of the oil film can be measured by measuring the capacitance $C_b$ of the ball bearing, since $C_b$ is given by $$C_b = \epsilon_0 \epsilon_r A / h$$

where $\epsilon_r$ is the relative dielectric constant of the oil used, while A is the area under which the film of oil is regarded as being present. The area A may be referred to as the area of contact.

Figure 1:
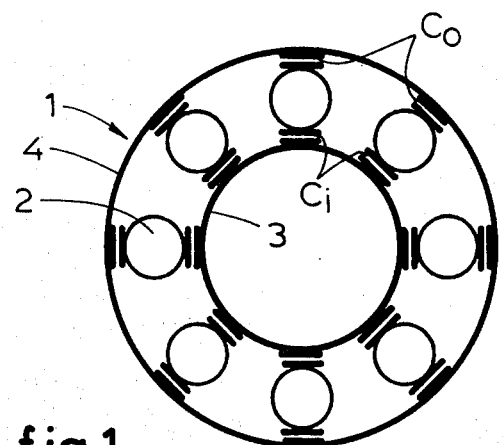
FIG. 1 schematically shows a ball bearing, indicating the capacitances present.

FIG. 1 shows a ball bearing 1 in which the various capacitances occurring between the balls 2 and the inner race 3 and outer race 4 are schematically indicated. These capacitances $C_i$ and $C_o$ together form the capacitance $C_b$ of the bearing:

$$C_b = \sum_{n=8} \frac{C_{in} \times C_{on}}{C_{in} + C_{on}}$$

Figure 2:
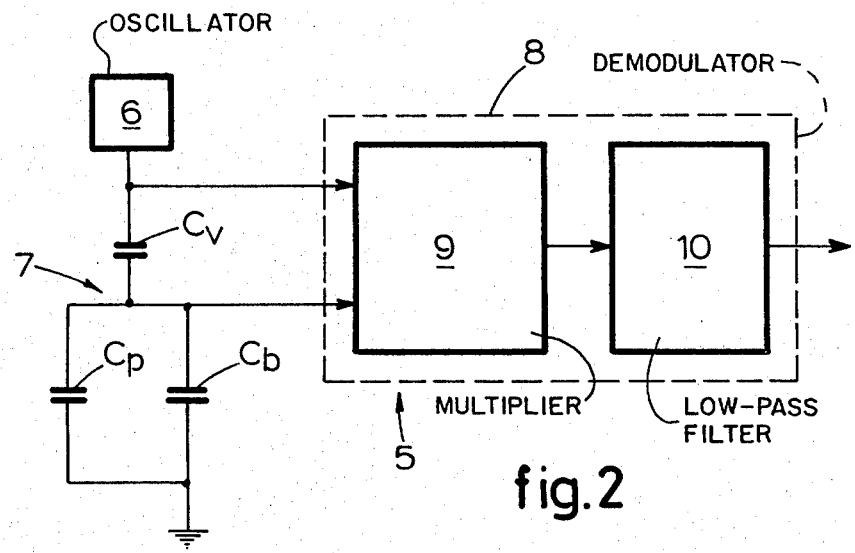
FIG. 2 is a block diagram of a portion of an embodiment of the device according to the invention.

FIG. 2 shows a device 5 by means of which the variation of the capacitance $C_b$ can be measured. The device 5 is equipped with an oscillator 6 delivering a sinusoidal AC voltage having a frequency of 0.9 MHz, for example, to a capacitive voltage divider 7, consisting of the capacitance $C_b$ and a condenser $C_v$. In parallel with the capacitance $C_b$, the total parasite capacitance $C_p$ is indicated as well. The voltage $V_b$ across the capacitance $C_b$ is now to be modulated by the variation in the value of the capacitance $C_b$. This modulating signal is derived from the voltage $V_b$ by means of a demodulator 8, provided with a multiplier 9 and a low-pass filter 10. The two inputs of the multiplier 9 and a low-pass filter 10. The two inputs of the multiplier 9 are respectively connected to the output of the oscillator 6 and to the condenser $C_b$.

The demodulator 8 delivers an output signal $V_{LP}$ depending on the oil film thickness h and the time t:

$$V_{LP} = f(h,t)$$

When direct contact occurs between the lubricated surfaces (h=0), the signal $V_{LP}$ will become at least approximately zero. From the signal $V_{LP}$, therefore, the percentage contact time during a time interval of measurement can be derived, while by a suitable processing of the signals, signals can be formed that depend linearly on the oil film thickness h and the capacitance $C_b$ respectively.

Figure 3:
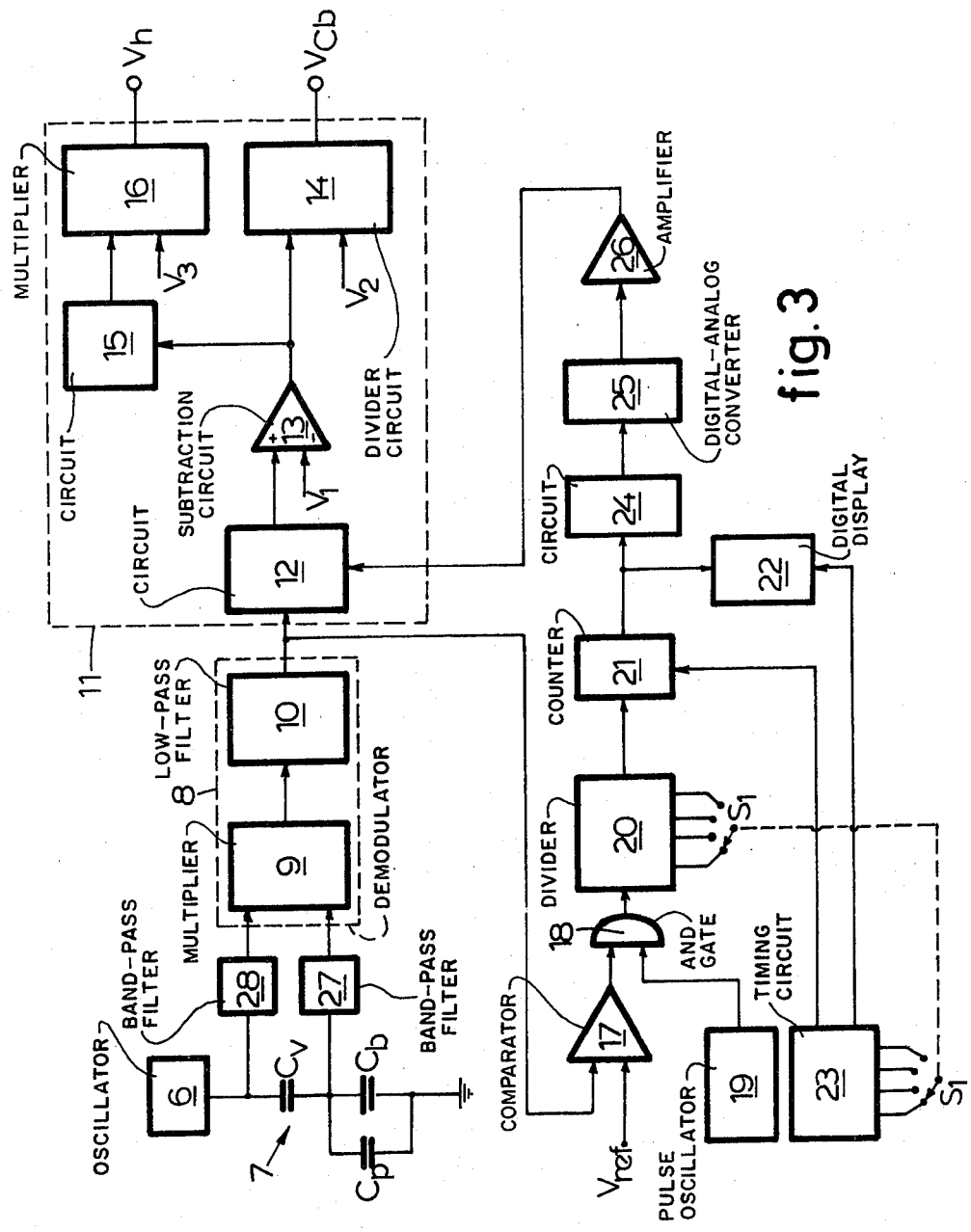
FIG. 3 is a block diagram of an embodiment of the device according to the invention.

FIG. 3 shows an embodiment of the device 5 delivering output signals $V_h$ and $V_{Cb}$ corresponding to the oil film thickness h and the capacitance $C_b$. The operation of the device may be further explained as follows.

When the oscillator 6 delivers an output voltage $V_{osc}$ sin $\omega t$, the voltage across the capacitance $C_b$ is given by $$V_b = \frac{V_{osc} C_v}{C_v + C_p + C_b},$$

whence it follows that the output voltage of the low-pass filter 10 is $$V_{LP} = \frac{(V_{osc})^2}{2} \cdot \frac{C_v}{C_v + C_p + C_b} \quad (1)$$

From this signal $V_{LP}$, a circuit 11 forms the desired signals $V_h$ and $V_{Cb}$. For this purpose, the output of filter 10 is connected to a circuit 12 whose output signal $V_o$ corresponds to the reciprocal of $V_{LP}$. The signal $V_o$ is therefore given by $$V_o = K_1 + K_2 C_b$$

where $$K_1 = \frac{2}{(V_{osc})^2} (1 + C_p/C_v)$$

and $$K_2 = \frac{2}{(V_{osc})^2} 1/C_v$$

It is assumed that the amplitude of the output voltage $V_{osc}$ of the oscillator 6, the condenser $C_v$, and the total parasite capacitance $C_p$, constant, so that the factors $K_1$ and $K_2$ may be represented by a constant voltage $V_1$ and $V_2$ respectively.

The signal $V_o$ is supplied to a subtraction circuit 13 reducing the signal $V_o$ by the quantity $V_1$. The output of circuit 13 is connected to a divider circuit 14 to which the voltage $V_2$ is also presented, so that the desired voltage $V_{Cb}$ appears at the output of the divider circuit 14.

The output of the subtraction circuit 13 is connected further to a circuit 15 forming the reciprocal of the output signal of the former circuit. The output of circuit 15 is connected to a multiplier 16 multiplying the output signal of circuit 15 by a constant factor, such that:

$$V_3 = o_r A K_2$$

The multiplier 16 therefore supplies the signal $V_h$ corresponding to the oil film thickness h.

The signals $V_h$ and $V_{Cb}$ may for example be reproduced on an oscilloscope, so that the behavior of the oil film thickness h and capacitance $C_b$ as functions of time can be observed. It is also possible to represent only the low-frequency component of the signals $V_h$ and $V_{Cb}$, so that only the slow variation in oil film thickness h and capacitance $C_b$ will be visible.

Figure 4B:
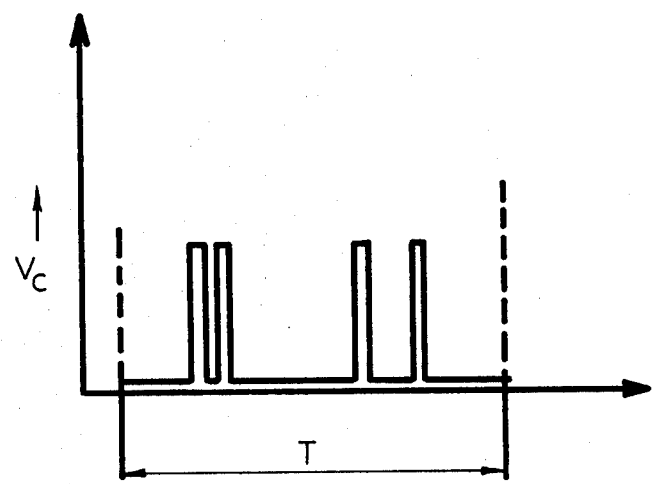
FIGS. 4a and 4b show two signals occurring in the device of FIG. 3.
Figure 4A:
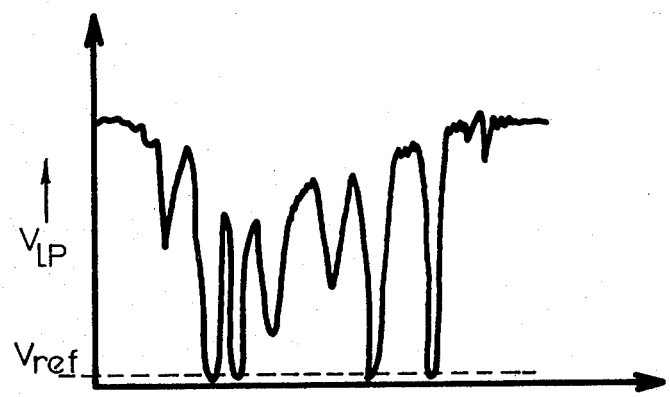

The percentage contact time may likewise be derived from the output signal $V_{LP}$ of filter 10. The output of filter 10 is for this purpose connected to the one input of a comparator 17, the other input of which is connected to an adjustable reference voltage $V_{ref}$. FIG. 4a shows an example of the output signal $V_{LP}$, with the reference voltage $V_{ref}$ also indicated. The reference voltage $V_{ref}$ is set to a small value. The output voltage $V_c$ of the comparator 17 passes from the low to the high level when the signal $V_{LP}$ falls below the reference voltage $V_{ref}$. The said voltage $V_c$ is represented in FIG. 4b. The output of the comparator 17 is connected to the first input of an AND gate 18, the second input of which is connected to a pulse oscillator 19 having a frequency of 1 MHz for example. The output of the AND gate 18 is connected by way of a divider 20 with adjustable divisor to a counter 21 controlling a digital display 22. The counter 21 thus counts the number of pulses passed through the AND gate 18 during the periods in which the output signal $V_c$ is high.

The circuit according to FIG. 3 is controlled by a timing circuit 23 determining an interval T after which the counter 21 is set back to zero. The frequency of the oscillator 19 and the length of the interval T are so chosen that the display 22 can reach a maximum reading of 99.999, should the signal $V_{LP}$ be smaller than the reference voltage $V_{ref}$ throughout the entire interval T. The display 22 thus indicates the percentage contact time for the interval T.

The interval T is adjustable by means of a switch $S_1$, which also sets the divisor of the divider 20, so that for each interval, the display 22 can attain a maximum reading of 99.999% at the selected oscillator frequency. After elapse of each interval T, the timer 21 is set back to zero by the timing circuit 23, whereupon a new interval is begun. The display 22 may of course be so controlled that a continuous indication is maintained. In measuring the state of lubrication of a ball bearing, the interval T may for example coincide with the time required for one revolution.

It has been found that when measuring the oil film thickness h at low values of $\lambda$, where $\lambda$ is the ratio between the oil film thickness and the surface rugosity, a smaller film thickness is registered than the value theoretically to be expected. This is due to the fact that the average oil film thickness measured is sharply diminished by the comparatively large number of direct contacts taking place between the lubricated surfaces.

Because the device according to the invention also measures the percentage contact time, the measurement of the oil film thickness h and capacitance $C_b$ can be corrected, obtaining a more accurate result of measurement of the thickness of the oil film. This correction may be carried out in various ways. It is possible for example to have the percentage contact time influence the output signals $V_{Cb}$ and $V_h$ directly.

An alternative possibility is schematically indicated in FIG. 3. A circuit 24 forms the complement of the percentage contact time, which complement is converted by a digital-analog converter 25 into an analog voltage. This analog voltage is amplified by a factor A by means of an amplifier 26, the output of the amplifier 26 controlling the circuit 12 that supplies the reciprocal of $V_{LP}$ as output signal. The signal $V_o$ is thereby corrected, so that the output signals $V_h$ and $V_{Cb}$ are corrected simultaneously. The factor A depends on the set reference voltage $V_{ref}$ for the comparator 17. This reference voltage corresponds to a certain maximum capacitance attained by the quantity $C_b$ upon occurrence of metal-to-metal contact.

The circuit 12 may for example be a circuit whose output signal $V_o$ is equal to $$\frac{10Y}{9}(Z/X)^m.$$

The output of the amplifier 26 is then connected to input Y and the output of filter 10 to input X, while the factor m is set to a value of one and the input Z is placed at a suitable constant voltage.

The voltage $V_b$ across the capacitance $C_b$ may contain a component of interference from the network frequency, disrupting the proper operation of the device. This difficulty is eliminated in the embodiment of the device according to the invention as shown by way of example in FIG. 3 by supplying the voltage $V_b$ to the demodulator 8 by way of a band-pass filter 27 tuned to the oscillator frequency. The output signal of the oscillator 6 is delivered to the demodulator 8 by way of a similar band-pass filter 28 to maintain a correct phase relationship between the input signals of the demodulator 8.

The invention is not limited to the embodiment described in the foregoing by way of example, which may be modified in various ways without departing from the idea of the invention.

We claim:

1. Device for measuring the lubrication of surfaces rolling or sliding relative to each other and lubricated by a lubricant, provided with an oscillator generating an AC voltage signal by means of which the capacitance occurring between the lubricated surfaces is measured, characterized in that the said capacitance is first grounded and then connected by way of a condenser to the output of the oscillator, which output is connected further to a first input of a demodulating circuit, while the voltage occurring across the capacitance is delivered to a second input of the demodulating circuit, the output of the demodulating circuit being connected to a processing unit that derives a signal corresponding to the thickness of the lubricant film as well as the percentage contact time during a certain interval of measurement from the output signal of the demodulating circuit.

2. Device according to claim 1, characterized in that the demodulating circuit consists of a multiplier and a low-pass filter connected to the output of the multiplier.

3. Device according to claim 1, characterized in that the processing unit is provided with a circuit forming the reciprocal of the output signal of the demodulating circuit as well as with first means connected to the output of the reciprocal circuit and delivering an output signal corresponding to the capacitance occurring between the lubricated surfaces.

4. Device according to claim 3, characterized in that the processing unit is provided with second means converting the measured percentage contact time into a correction signal supplied to a second input of the reciprocal circuit, in such manner that which increasing percentage contact time, the output signal of the reciprocal circuit decreases.

5. Device according to claim 3, characterized in that the said first means comprise a subtraction circuit the positive input of which is connected to the output of the reciprocal circuit while the negative input is placed at a predetermined constant voltage, the output being connected to a second reciprocal circuit whose output is connected to the input of a multiplier, the second input of the multiplier being placed at a second predetermined constant DC voltage, in such manner that the output signal of the multiplier corresponds to the thickness of the lubricant film.

6. Device according to claim 5, characterized in that the said first means further comprise a divider circuit one input of which is connected to the output of the subtraction circuit while the other input is placed at a third predetermined constant DC voltage, such that the output signal of the divider circuit corresponds to the capacitance occurring between the lubricated surfaces.

7. Device according to claim 1, characterized in that the processing unit is provided with a comparator one input of which is connected to the output of the demodulating circuit and the other input to a reference voltage, while the output is connected to one input of an AND gate the second input of which is connected to a pulse oscillator, the output of the AND gate being connected to a counter the output of which controls a digital display, where a timing means determines an interval of measurement after elapse of which said means sets the counter back to zero and starts a new interval of measurement, so that the final reading of the counter likewise corresponds to the percentage contact time during the interval of measurement in question.

8. Device according to claim 7, characterized in that the length of the interval of measurement is adjustable, the AND gate being connected to the counter by way of a divider circuit whose divisor increases in proportion to the prolongation of the interval of measurement.

9. Device according to claim 1, characterized in that the voltage occurring across the capacitance present between the lubricated surfaces is delivered to the demodulating circuit by way of a band-pass filter tuned to the oscillator frequency.

10. Device according to claim 9, characterized in that the oscillator is connected to the demodulating circuit by way of a band-pass filter tuned to the oscillator frequency.

11. Device according to claim 4, characterized in that the said second means comprise a means forming the complement of the percentage contact time, which complement is converted by a digital-analog converter into an analog signal supplied to the input of an amplifier, whose output delivers the correction signal.

* * * * *